(12) United States Patent
Igawa et al.

(10) Patent No.: US 7,923,129 B2
(45) Date of Patent: Apr. 12, 2011

(54) CARBAZOLE DERIVATIVE AND ORGANIC LIGHT EMITTING DEVICE USING THE SAME

(75) Inventors: Satoshi Igawa, Fujisawa (JP); Shinjiro Okada, Kamakura (JP); Takao Takiguchi, Chofu (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 675 days.

(21) Appl. No.: 11/946,206

(22) Filed: Nov. 28, 2007

(65) Prior Publication Data
US 2008/0131731 A1 Jun. 5, 2008

(30) Foreign Application Priority Data
Dec. 5, 2006 (JP) .................... 2006-328340

(51) Int. Cl.
H01J 1/62 (2006.01)
C07D 209/86 (2006.01)
C07D 401/02 (2006.01)
C07D 403/02 (2006.01)

(52) U.S. Cl. .................. 428/690; 428/917; 546/276.7; 548/446; 313/504; 313/506

(58) Field of Classification Search ............... None
See application file for complete search history.

(56) References Cited

U.S. PATENT DOCUMENTS

| | | | | |
|---|---|---|---|---|
| 6,649,772 B2 * | 11/2003 | Lin et al. | ......... | 548/439 |
| 7,282,275 B2 * | 10/2007 | Wolk et al. | ......... | 428/690 |
| 2003/0219625 A1 * | 11/2003 | Wolk et al. | ......... | 428/690 |
| 2004/0131881 A1 * | 7/2004 | Zheng et al. | ......... | 428/690 |
| 2008/0166591 A1 * | 7/2008 | Yamada et al. | ......... | 428/690 |

OTHER PUBLICATIONS

Chemical Physics Letters, vol. 408, No. 1-3, pp. 169-173, (2005).*
C.W. Tang et al., "Organic electroluminescent diodes", Appl. Phys. Lett. 51 (12), pp. 913-915, Sep. 21, 1987.
K. Burnner, et al., "Cabazole Compounds as Host Materials for Triplet Emitters in Organic Light-Emitting Diodes: Tuning the HOMO Level without Influencing the Triplet Energy in Small Molecules", J. Am. Chem. Soc., pp. 6035-6042 (2004).
J.W. Cheon, et al., "Chemiluminescent Properties of Novel Biphenyl Analogue Blue Fluorophores", Bull. Korean Chem. Soc., vol. 25, No. 8, pp. 1202-1206, Jun. 1, 2004.
U.S. Appl. No. 11/964,132, Confirmation No. 1321, filing date Dec. 26, 2007.
U.S. Appl. No. 11/913,054, Confirmation No. 5894, filing date Oct. 29, 2007.
U.S. Appl. No. 11/913,046, Confirmation No. 5813, filing date Oct. 29, 2007.

* cited by examiner

*Primary Examiner* — Dawn Garrett
(74) *Attorney, Agent, or Firm* — Fitzpatrick, Cella, Harper & Scinto

(57) ABSTRACT

Provided is an organic light emitting device including: a pair of electrodes including an anode and a cathode; and at least one layer formed of an organic compound interposed between the pair of electrodes, in which the at least one layer formed of the organic compound layer contains at least one kind of the carbazole derivative represented by the following general formula (I). The organic light emitting device has an optical output with extremely high efficiency and a high luminance and has an extremely high durability.

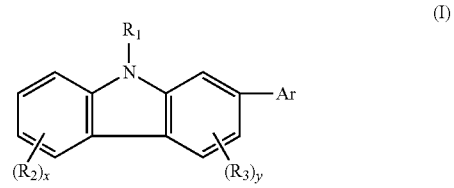

(I)

5 Claims, 3 Drawing Sheets

CARBAZOLE DERIVATIVE AND ORGANIC LIGHT EMITTING DEVICE USING THE SAME

BACKGROUND OF THE INVENTION

1. Field of the Invention

The present invention relates to a carbazole derivative and an organic light emitting device using the same.

2. Description of the Related Art

An organic light emitting device is a device in which a thin film including a fluorescent organic compound or a phosphorescent organic compound is interposed between an anode and a cathode. Further, electrons and holes are injected from the respective electrodes to generate exciton of the fluorescent compound or the phosphorescent compound, whereby light is emitted when the exciton return to a ground state is utilized.

According to a study at Eastman Kodak company in 1987 (Appl. Phys. Lett. 51, 913 (1987)), there is reported a device having a function-separation type two-layer structure using ITO as an anode, a magnesium-silver alloy as a cathode, an aluminum quinolinol complex as an electron transporting material and a light emitting material, and a triphenylamine derivative as a hole transporting material. There has been reported a light emission of approximately 1,000 cd/m² at an applied voltage of approximately 10 V.

Recent progress of an organic light emitting device is remarkable, and the characteristics of the device enable a light emitting device with a high luminance at a low applied voltage, a variety of emission wavelengths, high-speed responsiveness, thin and light weight. From this fact, it is suggested that the device have potential to find use in a wide variety of applications.

However, the present situation calls for optical output with even higher luminance or high conversion efficiency. In addition, many problems still remain to be solved regarding durability against the change over time due to long-term use, deterioration caused by atmospheric gas containing oxygen, moisture, or the like. Further, when considering application to a full color display, the present art is still insufficient against problems relating to the needs for light emission of blue, green, and red with a high color purity.

To solve the above-mentioned problems, there is proposed to use a carbazole derivative as a material for the organic light emitting device. As examples of the organic light emitting device using the carbazole derivative, there are given devices disclosed in "Journal of the American Chemical Society (2004), 126(19), 6035-6042," and "Bulletin of the Korean Chemical Society (2004), 25(8), 1202-1206."

SUMMARY OF THE INVENTION

An object of the present invention is to provide a novel carbazole derivative. Another object of the present invention is to provide an organic light emitting device having an optical output with extremely high efficiency and a high luminance and having an extremely high durability. Further, still another object of the present invention is to provide an organic light emitting device that can be easily produced at a relatively low cost.

A carbazole derivative according to the present invention is a compound represented by the following general formula (I):

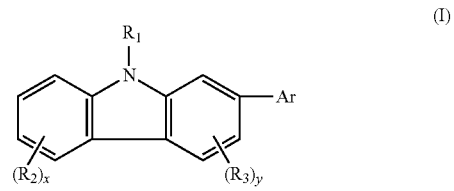

wherein $R_1$ represents a hydrogen atom, an alkyl group, a substituted or unsubstituted aralkyl group, a substituted or unsubstituted aryl group, or a substituted or unsubstituted heterocyclic group; $R_2$ and $R_3$ each represent an alkyl group, a substituted or unsubstituted aryl group, or a substituted or unsubstituted heterocyclic group; X represents an integer of 0 to 4, and y represents an inter of 0 to 3; when $R_2$ and/or $R_3$ exist in plural, the plurality of $R_2$ and/or $R_3$ may be the same or different; and Ar represents a substituted or unsubstituted condensed ring aromatic group having 4 or more rings.

The organic light emitting device of the present invention, which uses a carbazole derivative, is an excellent light emitting device because the organic light emitting device has not only an excellent light emission with high efficiency but also keep a high luminance for a longer period of time than that which uses the conventional compound.

Further features of the present invention will become apparent from the following description of exemplary embodiments with reference to the attached drawings.

DESCRIPTION OF THE EMBODIMENTS

Figure 1:
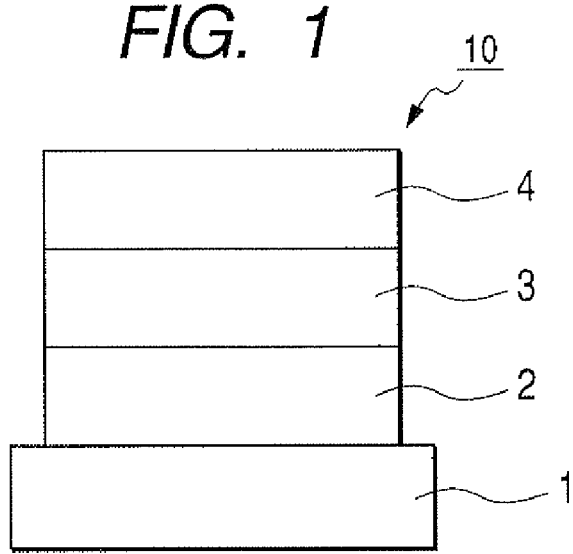
FIG. 1 is a sectional view illustrating a first embodiment of an organic light emitting device according to the present invention.

Hereinafter, the present invention will be described in detail.

First, description will be made of a carbazole derivative of the present invention. The carbazole derivative of the present invention is a compound represented by the following general formula (I):

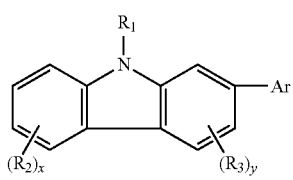

(I)

In the general formula (I), $R_1$ represents a hydrogen atom, an alkyl group, a substituted or unsubstituted aralkyl group, a substituted or unsubstituted aryl group, or a substituted or unsubstituted heterocyclic group.

Examples of the alkyl group represented by $R_1$, include a methyl group, an ethyl group, a normal propyl group, an isopropyl group, a normal butyl group, a tertiary butyl group, a hexyl group, an octyl group, a cyclohexyl group, and a trifluoromethyl group.

Examples of the aralkyl group represented by $R_1$ include a benzyl group and a phenethyl group.

Examples of the aryl group represented by $R_1$ include a phenyl group, a biphenyl group, a terphenyl group, a fluorenyl group, a naphthyl group, a fluorantenyl group, an anthryl group, a phenanthryl group, a pyrenyl group, a tetracenyl group, a pentacenyl group, a triphenylenyl group, and perylenyl group.

Examples of the heterocyclic group represented by $R_1$ include a thienyl group, a pyrrolyl group, a pyridyl group, an oxazolyl group, an oxadiazolyl group, a thiazolyl group, a thiadiazolyl group, and a terthienyl group.

Examples of substituents which the above-mentioned aralkyl group, aryl group, and heterocyclic group may have include: alkyl groups such as a methyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; alkoxyl groups such as a methoxyl group, an ethoxyl group, a propoxyl group, and a phenoxyl group; a cyano group; and halogen atoms such as fluorine, chlorine, bromine, and iodine.

In the general formula (I), $R_2$ and $R_3$ each represent an alkyl group, a substituted or unsubstituted aryl group, or a substituted or unsubstituted heterocyclic group.

Examples of the alkyl group represented by $R_2$ and $R_3$ include a methyl group, an ethyl group, a normal propyl group, an isopropyl group, a normal butyl group, a tertiary butyl group, a hexyl group, an octyl group, a cyclohexyl group, and a trifluoromethyl group.

Examples of the aryl group represented by $R_2$ and $R_3$ include a phenyl group, a biphenyl group, a terphenyl group, a fluorenyl group, a naphthyl group, a fluorantenyl group, an anthryl group, a phenanthryl group, a pyrenyl group, a tetracenyl group, a pentacenyl group, a triphenylenyl group, a perylenyl group, a benzofluorantenyl group, and a chrysenyl group.

Examples of the heterocyclic group represented by $R_2$ and $R_3$ include a thienyl group, a pyrrolyl group, a pyridyl group, an oxazolyl group, an oxadiazolyl group, a thiazolyl group, a thiadiazolyl group, a terthienyl group, a quinolyl group, and a carbazolyl group.

Examples of substituents which the above-mentioned aryl group and heterocyclic group may have include: alkyl groups such as a methyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; alkoxyl groups such as a methoxyl group, an ethoxyl group, a propoxyl group, and a phenoxyl group; a cyano group; and halogen atoms such as fluorine, chlorine, bromine, and iodine.

In the general formula (I), x represents an integer of 0 to 4.

In the general formula (I), y represents an integer of 0 to 3.

In the general formula (I), Ar represents a substituted or unsubstituted condensed ring aromatic group having 4 or more rings, preferably 4 or more to 7 or less rings. Specific examples of the condensed ring aromatic group include a pyrenyl group, a fluorantenyl group, a benzofluorantenyl group, a tetracenyl group, a pentacenyl group, a triphenylenyl group, a perylenyl group, a chrysenyl group, and a rubicenyl group.

Examples of substituents which the above-mentioned condensed ring aromatic group may have include: alkyl groups such as a methyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; alkoxyl groups such as a methoxyl group, an ethoxyl group, a propoxyl group, and a phenoxyl group; a cyano group; and halogen atoms such as fluorine, chlorine, bromine, and iodine.

Ar in the general formula (I) is preferably a pyrenyl group or a fluorantenyl group, in considering the use for a blue light emitting material and a host material, and more preferably a substituted or unsubstituted pyrenyl group represented by the general formula (II) below.

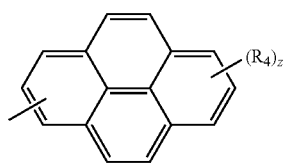

(II)

In the general formula (II), $R_4$ represents an alkyl group, a substituted or unsubstituted aralkyl group, a substituted or unsubstituted aryl group, a substituted or unsubstituted heterocyclic group, a substituted amino group, or a halogen atom.

Examples of the alkyl group represented by $R_4$ include a methyl group, an ethyl group, a normal propyl group, an isopropyl group, an normal butyl group, a tertiary butyl group, a hexyl group, an octyl group, a cyclohexyl group, and a trifluoromethyl group.

Examples of the aralkyl group represented by $R_4$ include a benzyl group and a phenethyl group.

Examples of the aryl group represented by $R_4$ include a phenyl group, a biphenyl group, a terphenyl group, a fluorenyl group, a naphthyl group, a fluorantenyl group, an anthryl group, a phenanthryl group, a pyrenyl group, a tetracenyl group, a pentacenyl group, a triphenylenyl group, and a perylenyl group.

Examples of the heterocyclic group represented by $R_4$ include a thienyl group, a pyrrolyl group, a pyridyl group, an oxazolyl group, an oxadiazolyl group, a thiazolyl group, a thiadiazolyl group, and a terthienyl group.

Examples of the substituted amino group represented by $R_4$ include a dimethylamino group, a diethylamino group, a dibenzylamino group, a diphenylamino group, a ditolylamino group, and a dianisolylamino group.

Examples of the halogen represented by $R_4$ include fluorine, chlorine, bromine, and iodine.

Examples of substituents which the above-mentioned aralkyl group, aryl group, and heterocyclic group may have include: alkyl groups such as a methyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; alkoxyl groups such as a methoxyl group, an ethoxyl group, a propoxyl group, and a phenoxyl group; a cyano group; and halogen atoms such as fluorine, chlorine, bromine, and iodine.

It should be noted that the substituted group represented by $R_4$ is preferably a bulky substituted group such as a tertiary butyl group from the view point of the intermolecular stacking suppression of a pyrenyl group.

The carbazole derivative represented by the general formula (I) is preferably a compound represented by the general formula (III).

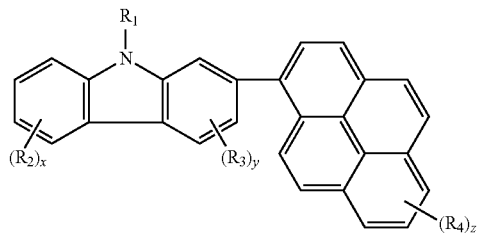

(III)

In the general formula (III), each of $R_1$, $R_2$, $R_3$, x, and y is the same as $R_1$, $R_2$, $R_3$, x, and y in the general formula (I), respectively, and $R_4$ and z are each the same as $R_4$ and z in the general formula (II).

Hereinafter, specific structural formulae of a carbazole derivative according to the present invention will be described in detail below. However, typical examples thereof are exemplified below, and the present invention is not limited these.

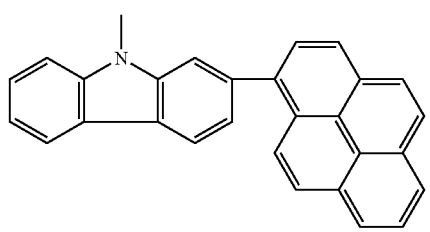

A-1

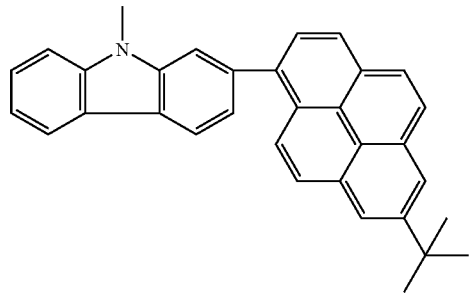

A-2

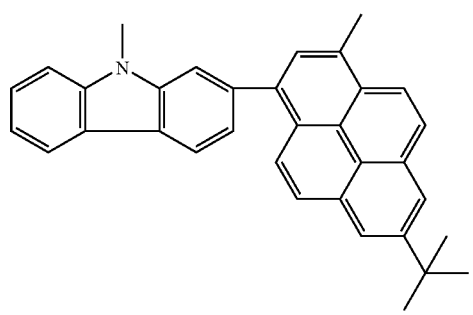

A-3

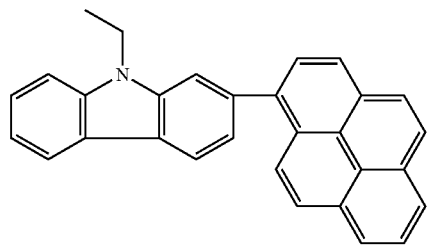

A-4

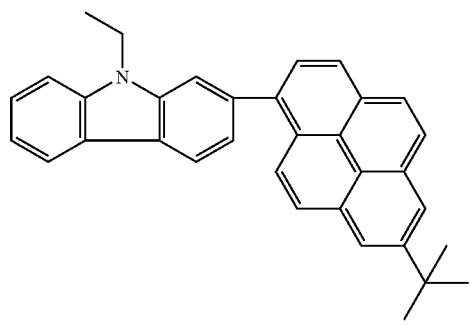

A-5

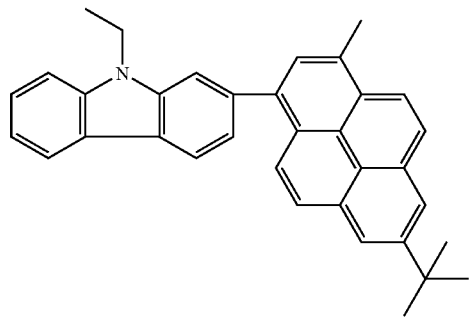

A-6

-continued
A-7
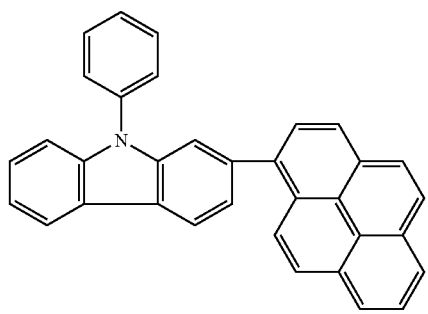
A-8
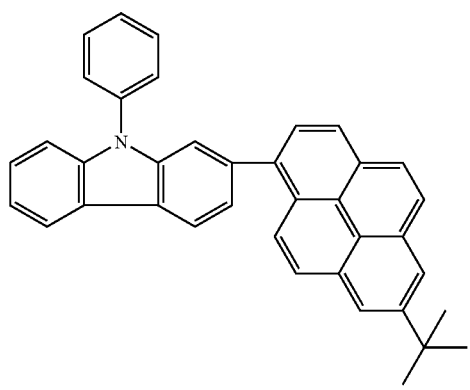
A-9
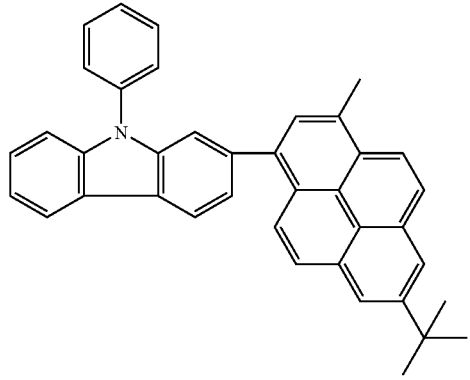
A-10
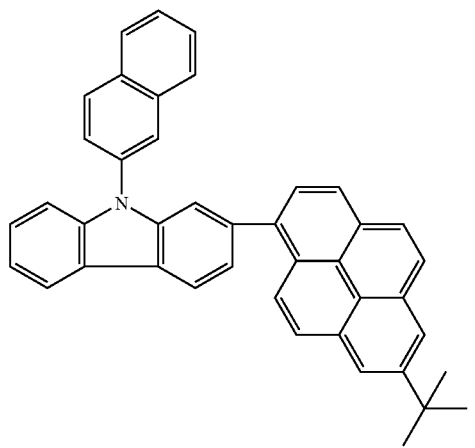
-continued
A-11
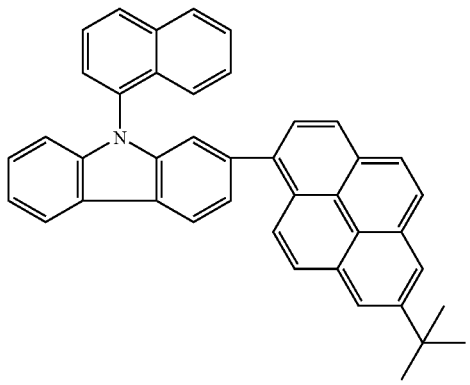
A-12
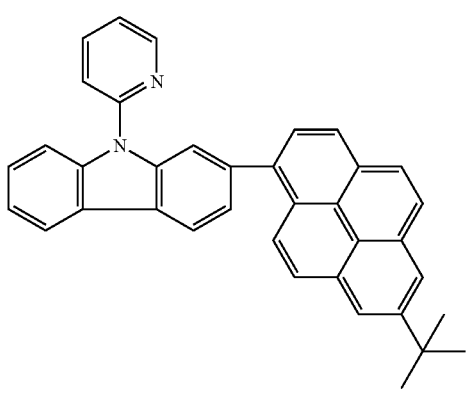
A-13
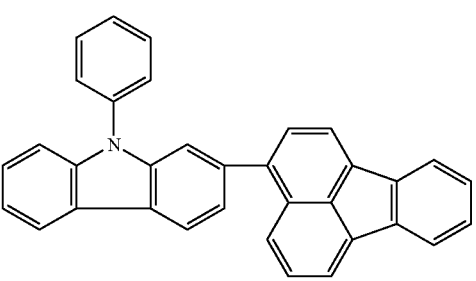
A-14
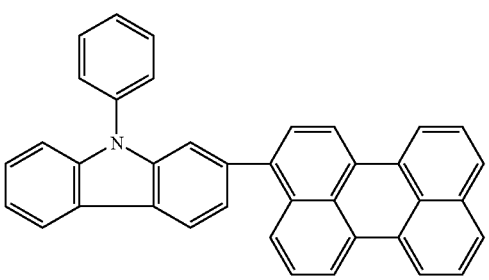

A-15
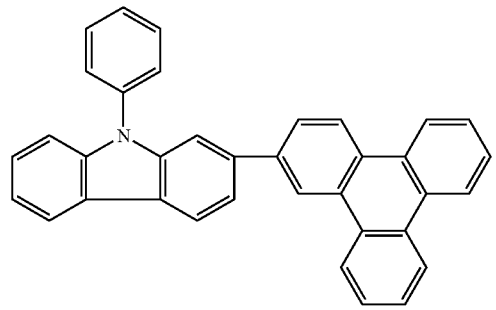
A-19
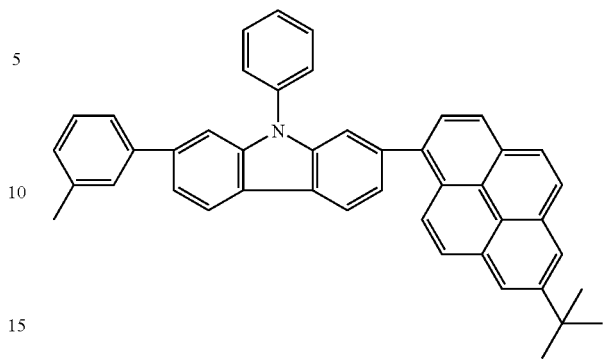
A-16
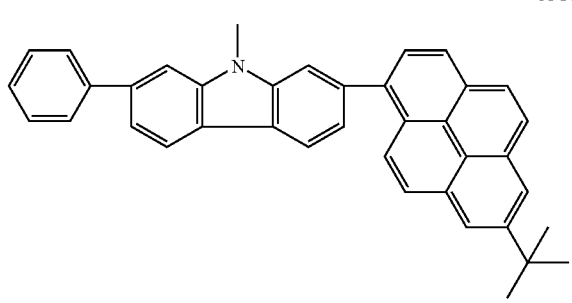
A-20
A-17
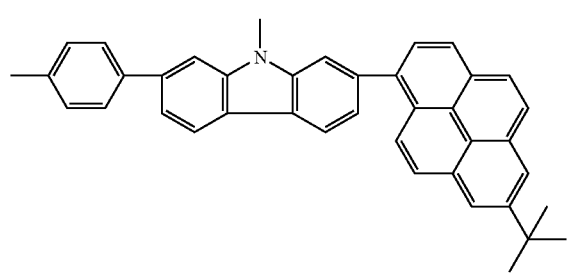
A-21
A-18
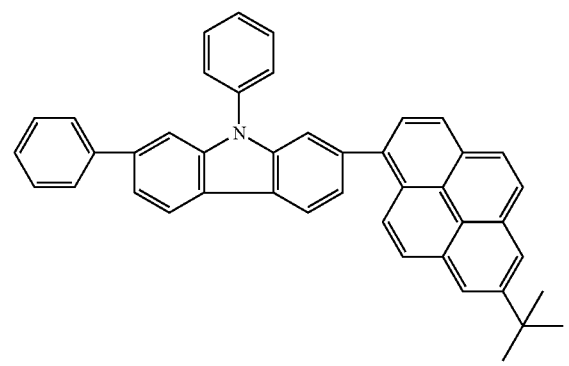
A-22
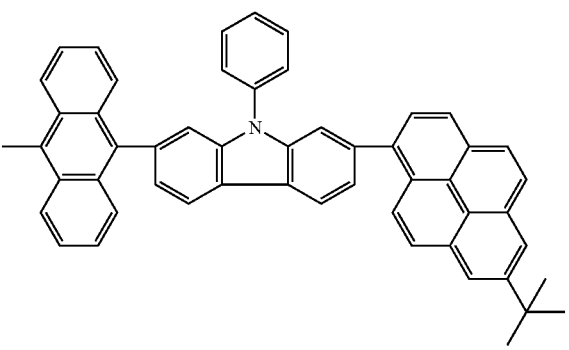

A-23
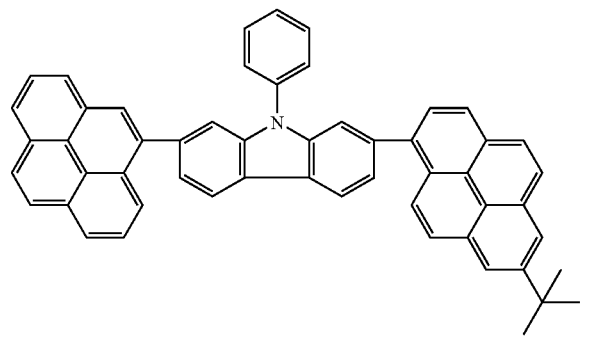
A-28
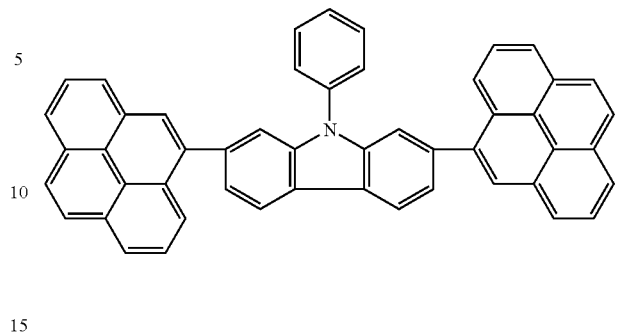
A-24
A-29
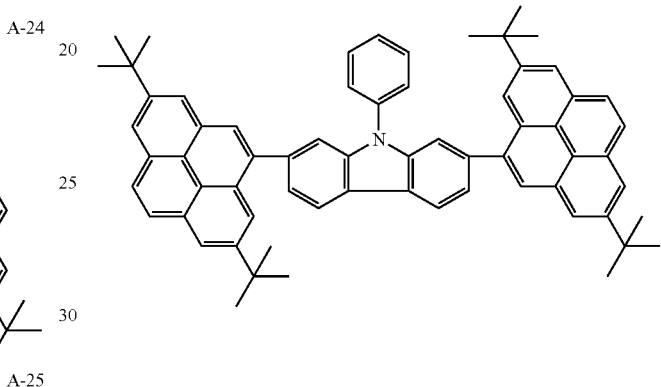
A-25
A-30
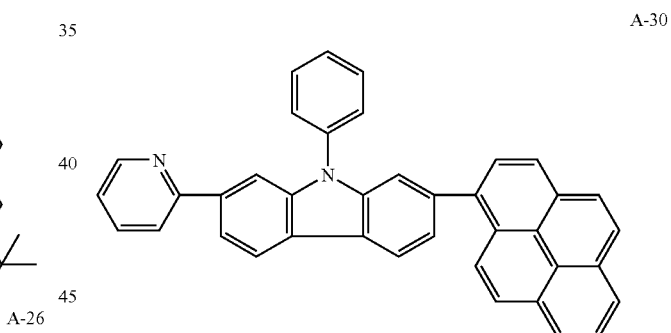
A-26
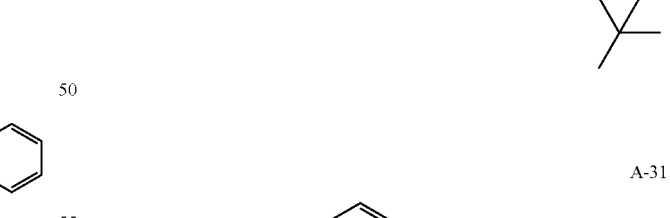
A-27
A-31
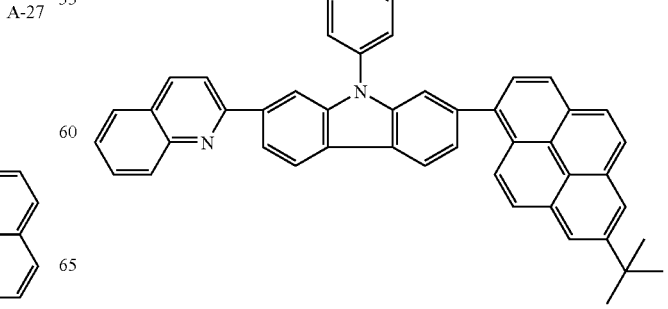

A-32
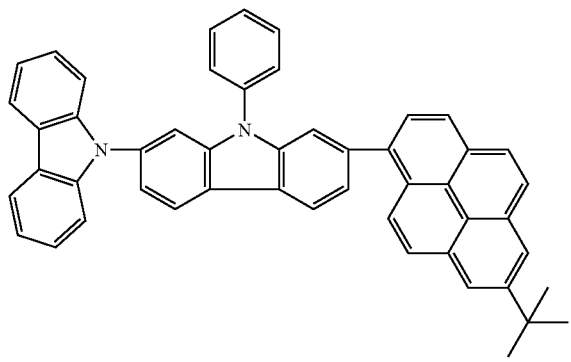

A-33
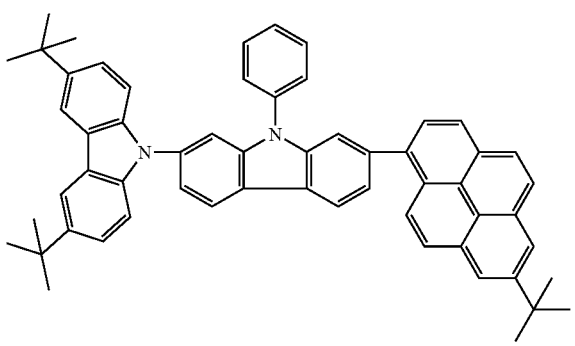

A-34
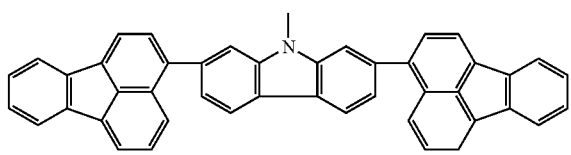

A-35
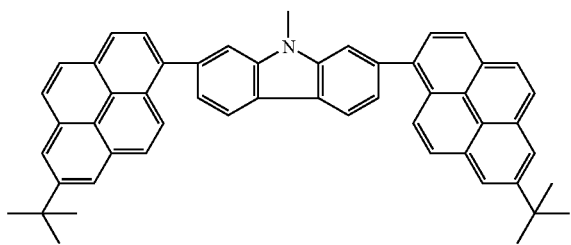

A-36
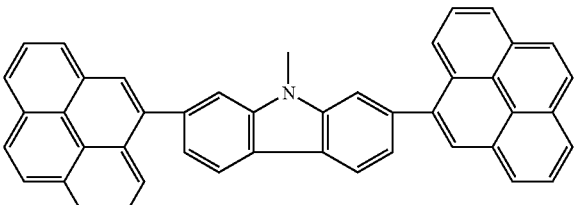

A-37
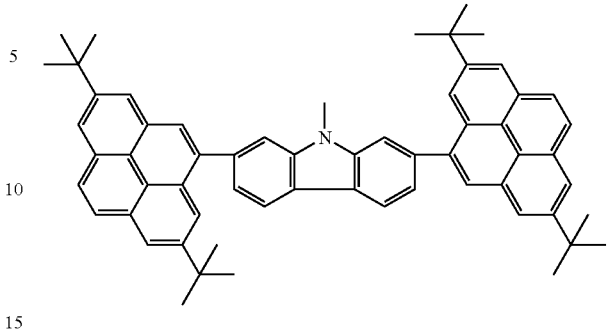

The organic light emitting device of the present invention includes: at least a pair of electrodes including an anode and a cathode; and at least one layer formed of an organic compound, the at least one of the layer being interposed between the pair of electrodes. In addition, in the light emitting device of the present invention, the at least one layer formed of the organic compound contains the carbazole derivative according to the present invention.

Hereinafter, an organic light emitting device of the present invention will be described in detail with reference to the drawings.

In FIGS. 1 to 6, reference Numeral 1 denotes a substrate; 2, an anode; 3, a light emitting layer; 4, a cathode; 5, a hole transporting layer; 6, an electron transporting layer; 7, a hole injecting layer; 8, a hole/exciton blocking layer; and 10, 20, 30, 40, 50, and 60 each denote an organic light emitting device.

FIG. 1 is a sectional view illustrating a first embodiment of an organic light emitting device according to the present invention. The organic light emitting device 10 of FIG. 1 includes the anode 2, the organic light emitting layer 3, and the cathode 4, which are sequentially formed on the substrate 1. The organic light emitting device 10 is useful in a case where the light emitting layer 3 is formed of a compound which has all the properties including a hole transporting ability, an electron transporting ability, and light emitting property or a case where the light emitting layer 3 is formed of a mixture of compounds each having one of the hole transporting ability, the electron transporting ability, and the light emitting property.

Figure 2:
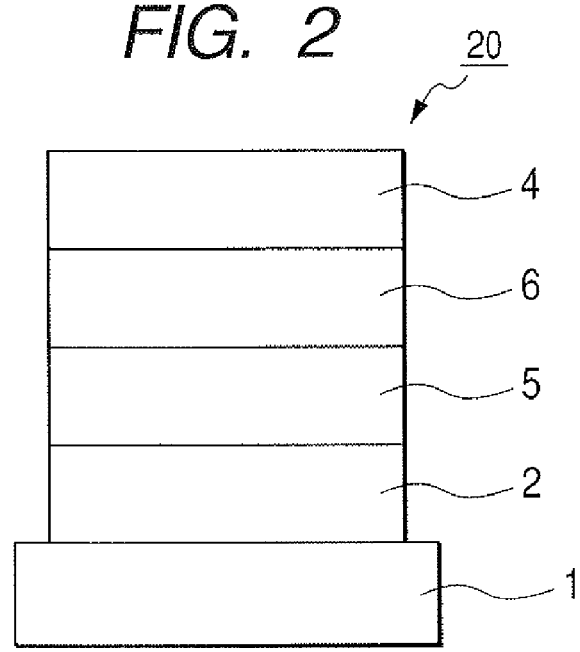
FIG. 2 is a sectional view illustrating a second embodiment of the organic light emitting device according to the present invention.

FIG. 2 is a sectional view illustrating a second embodiment of the organic light emitting device according to the present invention. The organic light emitting device 20 of FIG. 2 includes the anode 2, the hole transporting layer 5, the electron transporting layer 6, and the cathode 4, which are sequentially formed on the substrate 1. The organic light emitting device 20 is useful in a case where a light emitting compound having hole-transporting property and/or electron transporting property and an organic compound having electron transporting property alone or hole-transporting property alone are used in combination. In addition, in the light emitting layer 20, the hole transporting layer 5 or the electron transporting layer 6 serves as the light emitting layer.

Figure 3:
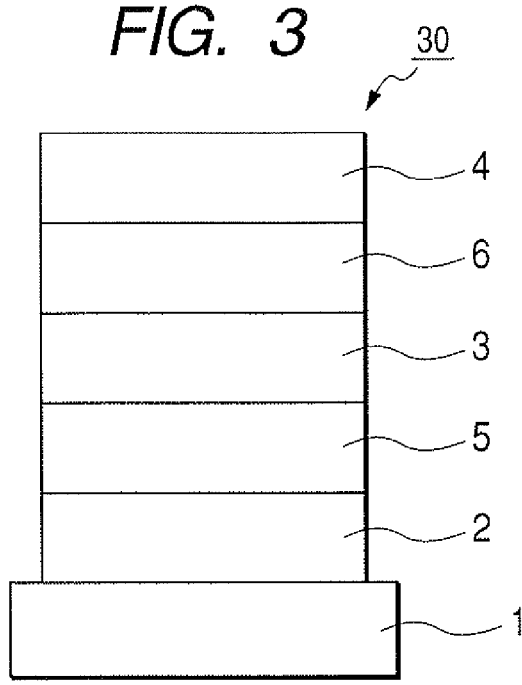
FIG. 3 is a sectional view illustrating a third embodiment of the organic light emitting device according to the present invention.

FIG. 3 is a sectional view illustrating a third embodiment of the organic light emitting device according to the present invention. The organic light emitting device 30 of FIG. 3 illustrate a structure in which the light emitting layer 3 is inserted between the hole transporting layer 5 and the electron transporting layer 6 in the organic light emitting device 30 of FIG. 2. In the organic light emitting device 30, a carrier-transporting function and a light-emitting function are separated from each other. Thus, the device can be used appropriately in combination with compounds each having one of the hole-transporting property, electron transporting property, and light emitting property. Therefore, the degree of freedom in selection of a material extremely increases as well as various compounds different from each other in emission wavelength can be used. As a result, the range of luminescent colors can be widened. Further, a light emitting efficiency can be improved by effectively trapping carrier or exciton in the light emitting layer 3.

Figure 4:
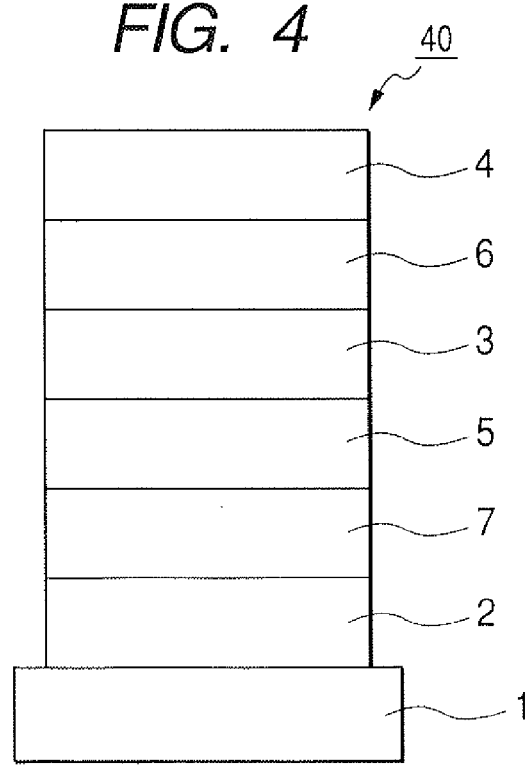
FIG. 4 is a sectional view illustrating a fourth embodiment of the organic light emitting device according to the present invention.

FIG. 4 is a sectional view illustrating a fourth embodiment of the organic light emitting device according to the present invention. The organic light emitting device 40 of FIG. 4 illustrate a structure in which the hole injecting layer 7 is provided between the anode 2 and the hole transporting layer 5 in the organic light emitting device 30 of FIG. 3. The provision of the hole injecting layer 7 in the organic light emitting device 40 imparts an improving effect on adhesiveness between the anode 2 and the hole transporting layer 5 or on hole injection property, and is effective for a reduction in voltage at which the device is driven.

Figure 5:
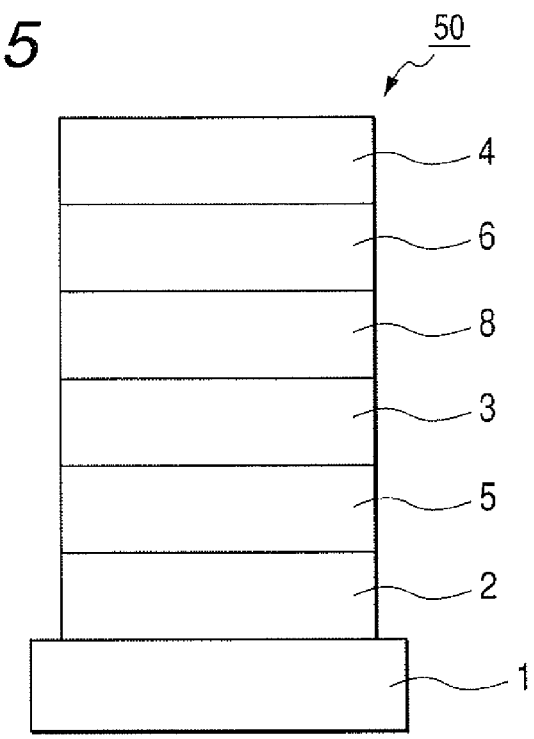
FIG. 5 is a sectional view illustrating a fifth embodiment of the organic light emitting device according to the present invention.

FIG. 5 is a sectional view illustrating a fifth embodiment of the organic light emitting device according to the present invention. The organic light emitting device 50 of FIG. 5 illustrate a structure in which a layer for inhibiting the escape of a hole or exciton toward the side of the cathode 4 side (hole/exciton blocking layer 8) is inserted between the light emitting layer 3 and the electron transporting layer 6 in the organic light emitting device 30 of FIG. 3. The provision of the organic compound having an extremely high ionization potential as the hole/exciton blocking layer 8 improves the light emitting efficiency of the organic light emitting device 50.

Figure 6:
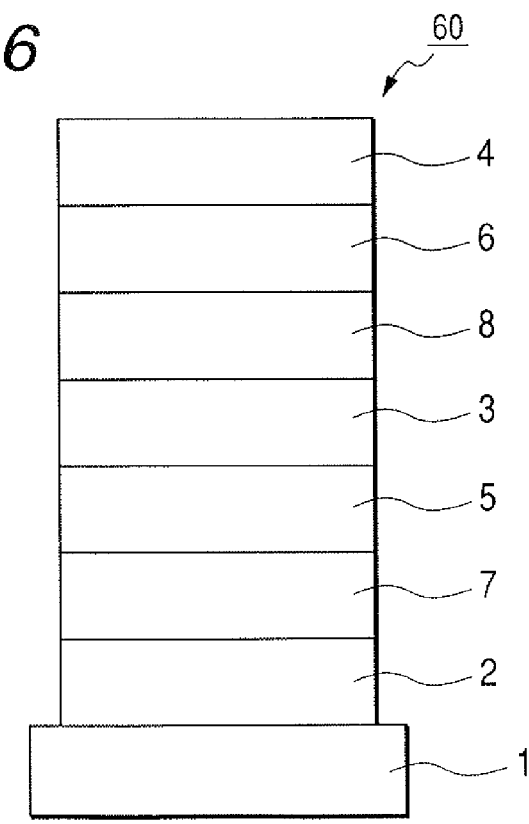
FIG. 6 is a sectional view illustrating a sixth embodiment of the organic light emitting device according to the present invention.

FIG. 6 is a sectional view illustrating a sixth embodiment of the organic light emitting device according to the present invention. The organic light emitting device 60 of FIG. 6 illustrate a structure in which the hole/exciton blocking layer 8 is inserted between the light emitting layer 3 and the electron transporting layer 6 in the organic light emitting device 40 of FIG. 4. The provision of the organic compound having an extremely high ionization potential as the hole/exciton blocking layer 8 improves the light emitting efficiency of the organic light emitting device 60.

It should be noted that the device structure illustrated in FIGS. 1 to 6 are each merely very basic one, and the structure of the organic light emitting device of the present invention is not limited to those. For example, an insulating layer may be provided onto an interface between an electrode and an organic layer. Alternatively, an adhesive layer or an interference layer may be provided thereonto. In addition, a hole transporting layer 5 may be formed of two layers having different ionization potentials.

In the organic light emitting devices shown in FIGS. 1 to 6, at least one of the light emitting layer 3, the hole transporting layer 5, the electron transporting layer 6, the hole transporting layer 7, and the hole/exciton blocking layer 8 contains at least one kind of the carbazole derivative of the present invention.

Preferably, the carbazole derivative of the present invention is contained in the light emitting layer 3. Besides, in the organic light emitting device of the present invention, the light emitting layer 3 is preferably formed of a host and a guest. In this case, the guest refers to a compound that emits light in response to recombination of the hole and the electron in the light emitting region of the organic light emitting device. In the organic light emitting device of the present invention, the host or guest is preferably the carbazole derivative of the present invention.

When the light-emitting layer is formed of a carrier-transporting host material and guest material, the main process for light emission includes the following several steps.
1. Transport of electron and hole in light-emitting layer
2. Production of exciton of host
3. Transfer of excitation energy between host molecules
4. Transfer of excitation energy from host to guest Desired energy transfer or light emission in each step occurs in competition with various deactivation steps.

It is needless to say that the light emitting quantum efficiency of a light emitting center material itself must be large in order to increase the light emitting efficiency of the organic light emitting device. Besides, the efficiency of energy movement between a host and another host or between a host and a guest is also a large problem to increase the light emitting efficiency of the organic light emitting device. In addition, to minimize the deterioration of light emission due to energization is also a problem to increase the light emitting efficiency of the organic light emitting device. The cause for the deterioration of light emission has not yet been clarified. However, the deterioration is probably related to at least environmental changes to a light emitting material due to the light emitting center material or molecules around the center material.

Therefore, the carbazole derivative of the present invention is used as a host or a guest constituting the light emitting layer. As a result, the light emitting efficiency of the organic light emitting device can be increased, a high luminance can be kept for a longer period of time, and the deterioration due to energization can be made small.

In a case where the carbazole derivative of the present invention is used as the guest, the content thereof is preferably 50 wt % or less, more preferably, from 0.1 wt % to 30 wt %, most preferably, from 0.1 wt % to 15 wt % with respect to the total weight of the organic compounds constituting the light emitting layer 3.

On the other hand, in a case where the carbazole derivative of the present invention is used as the host compound, there is no limitation about the guest. Accordingly, compounds described later can be appropriately used depending on the desired luminescent color, or the like. Further, the hole transporting compound, the electron transporting compound, or the like can be optionally used by doping those compounds together other than the guest. In the case where the carbazole derivative of the present invention is used as the host compound, the content thereof is preferably from 70 wt % to 99.9 wt % with respect to the total weight of the organic compounds constituting the light emitting layer 3.

As described above, the carbazole compound of the present invention may be used only for the light emitting layer. However, the carbazole compound of the present invention may be used for the hole injecting layer, the hole transporting layer, the electron injecting layer, the electron transporting layer, the electron barrier layer, and the like other than the light emitting layer.

The carbazole compound of the present invention is a compound excellent in electron transporting property, light emitting property, and durability compared with the conventional compound, and can be used in any mode as shown in FIGS. 1 to 6.

In the organic light emitting device of the present invention, the carbazole derivative of the present invention is used as a component of a hole transporting layer and a light emitting layer. However, the hole transporting compound, the light emitting compound, or the electron transporting compound, which are conventionally known may be used together with the compound as required.

Hereinafter, the hole transporting compound, the light emitting compound, the electron transporting compound, and the like are exemplified.
Hole transporting compound
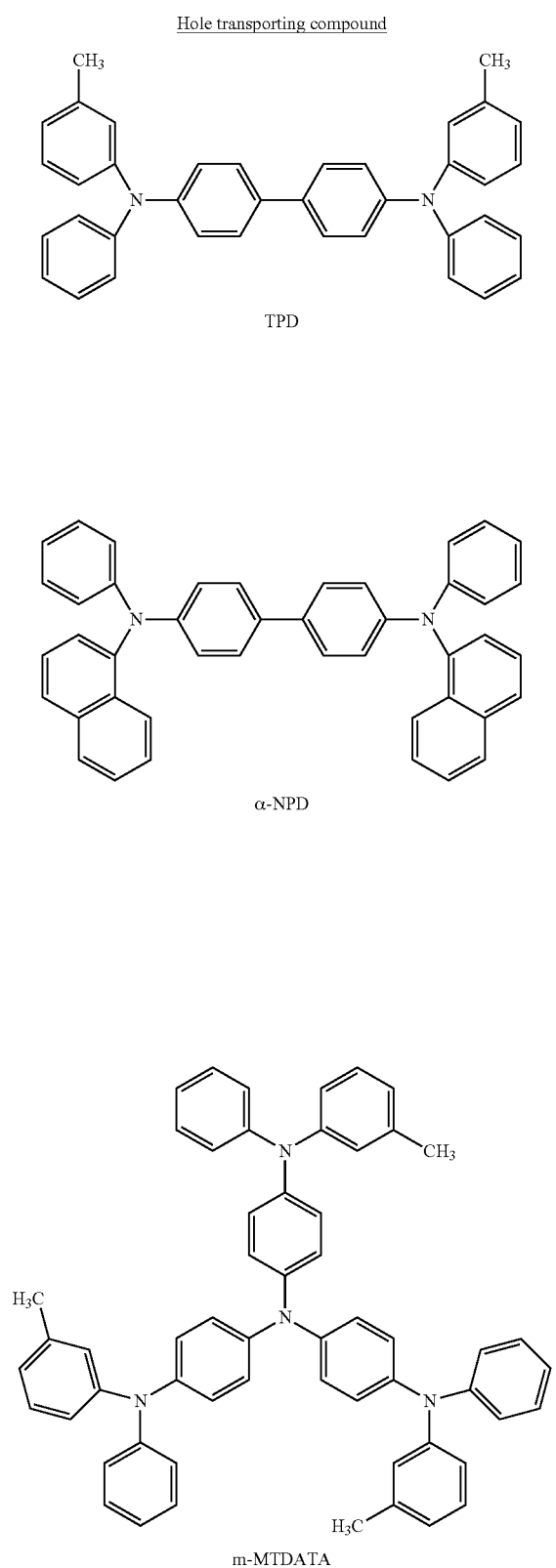
TPD
α-NPD
m-MTDATA
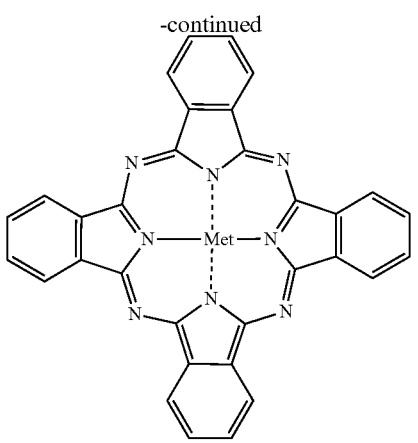
Met: Cu, Mg, AlCl, TiO, SiCl₂ etc
Met-Pc
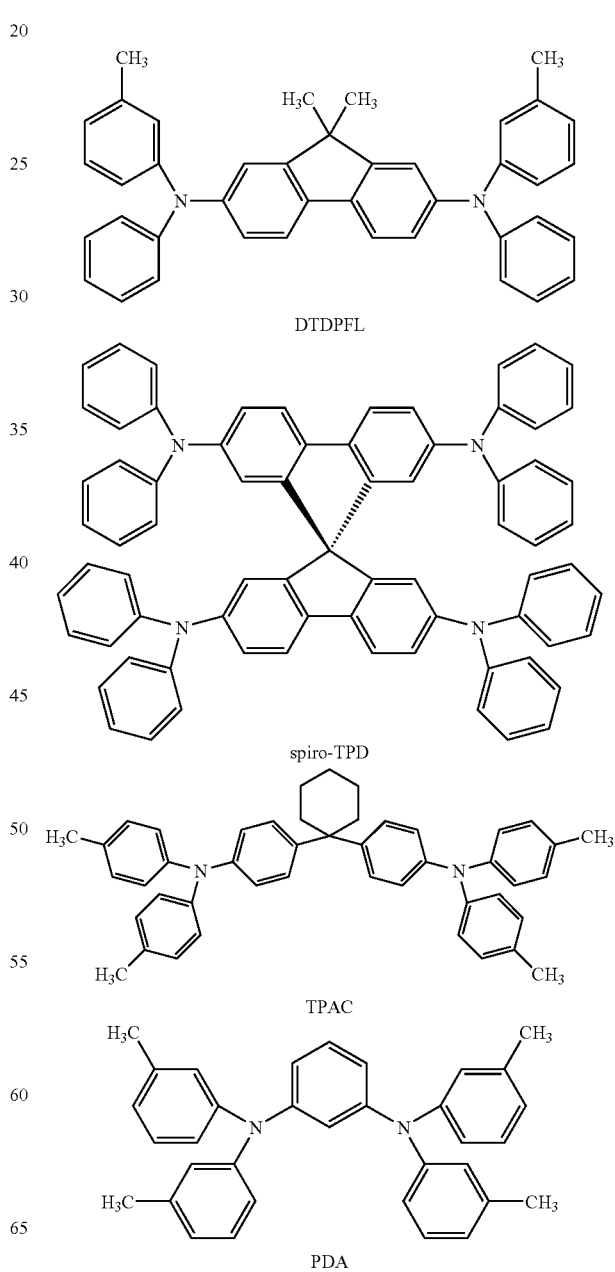
DTDPFL
spiro-TPD
TPAC
PDA Electron transporting light emitting material
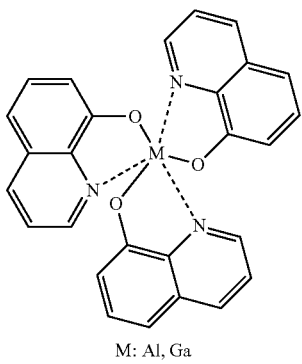
M: Al, Ga
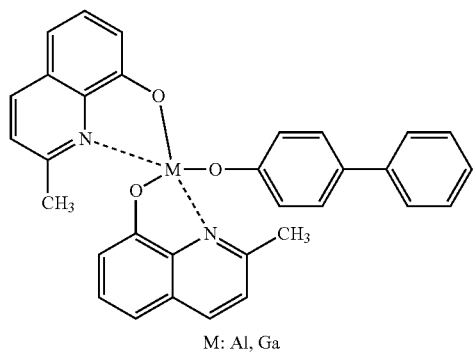
M: Al, Ga
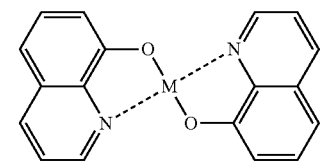
M: Zn, Mg, Be
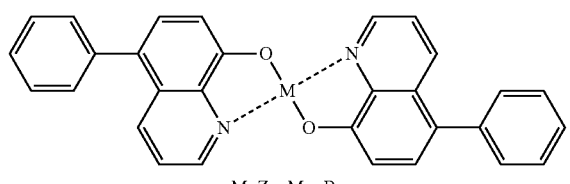
M: Zn, Mg, Be
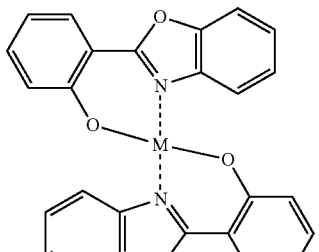
M: Zn, Mg, Be
-continued
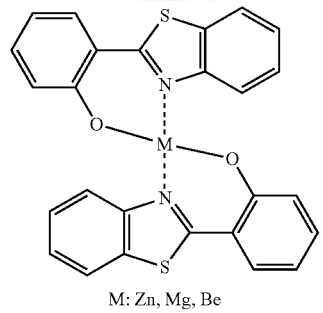
M: Zn, Mg, Be
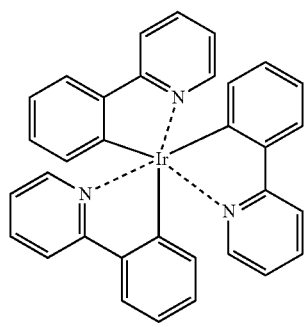
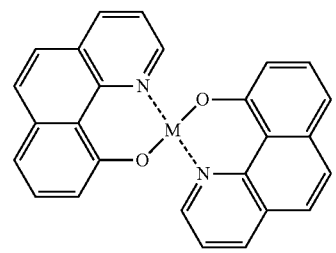
M: Zn, Mg, Be
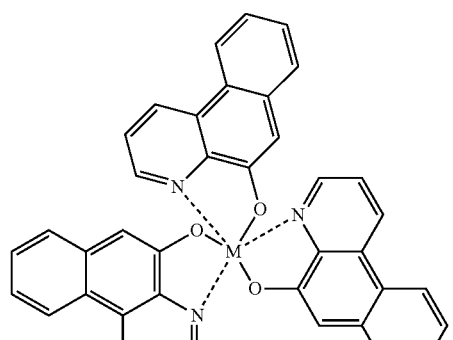
M: Al, Ga Light emitting material
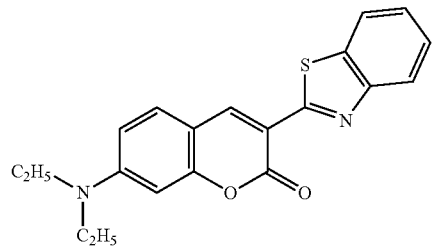
Coumarin6
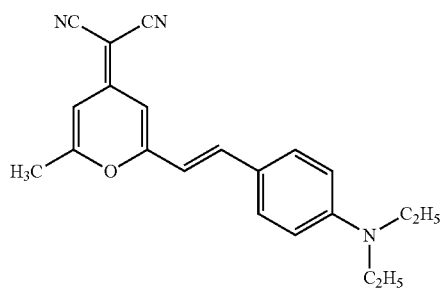
DCM-1
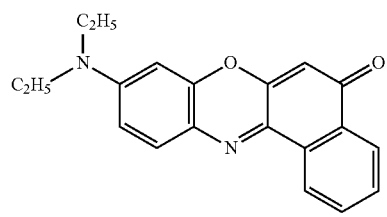
Nile red
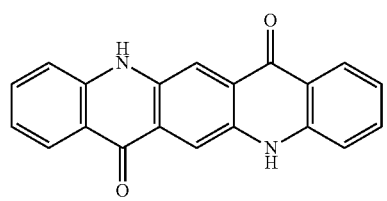
Quinacridone
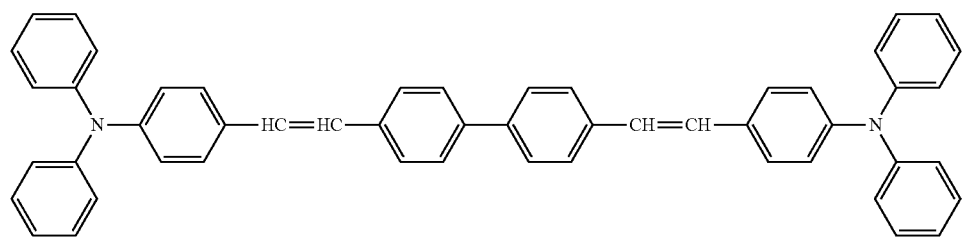
DPABVi
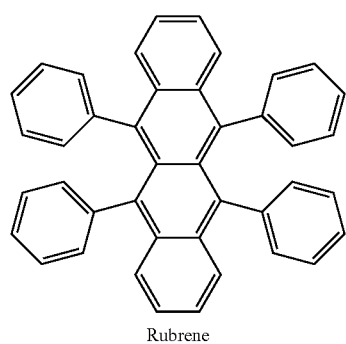
Rubrene
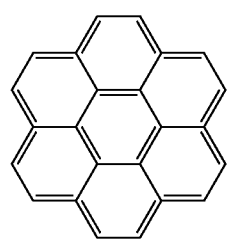
Coronene Light emitting layer matrix material and electron transporting material
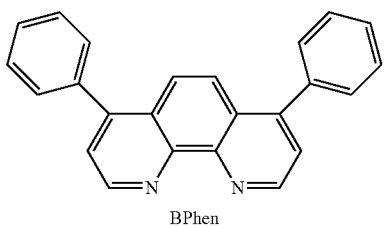
BPhen
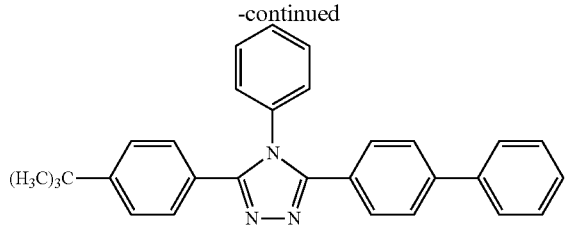
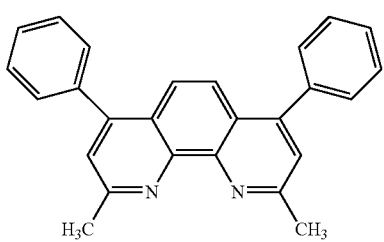
BCP
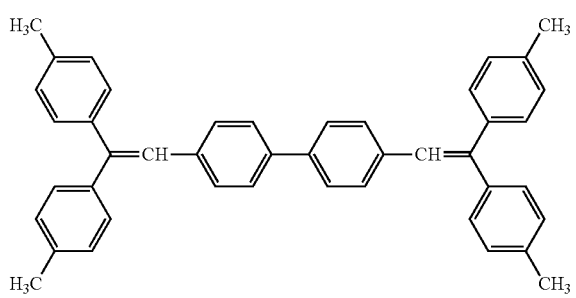
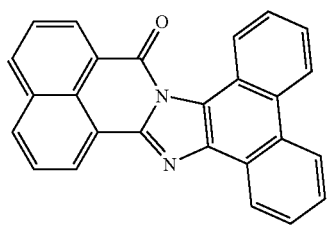
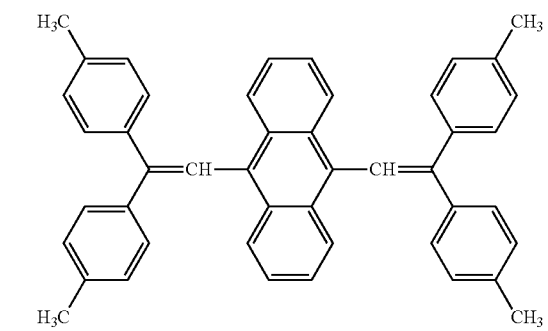
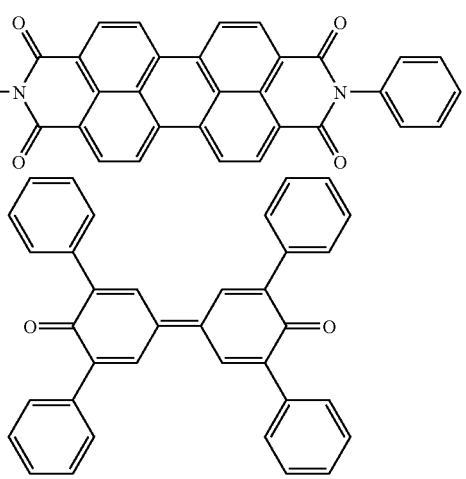
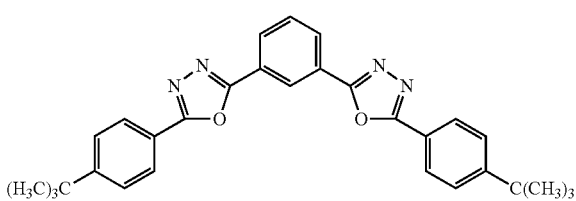

Polymer hole transporting material
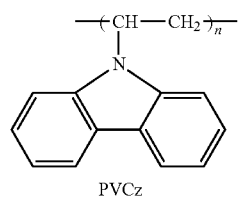
PVCz
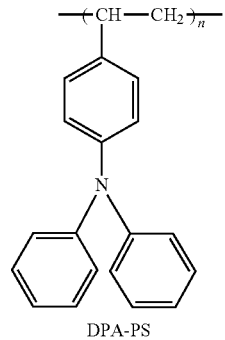
DPA-PS
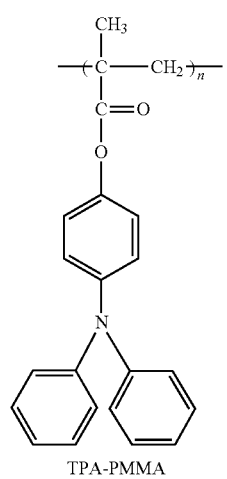
TPA-PMMA
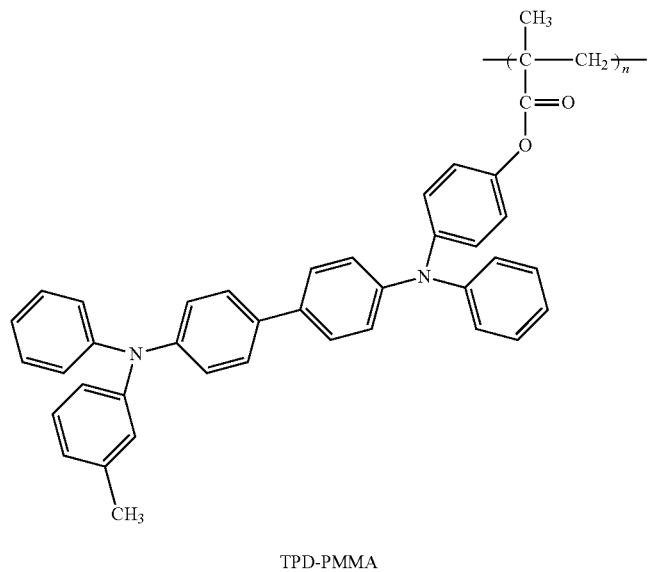
TPD-PMMA
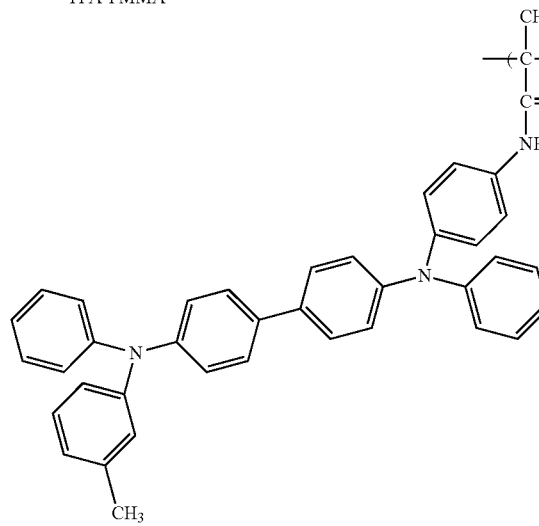
TPD-PMAA

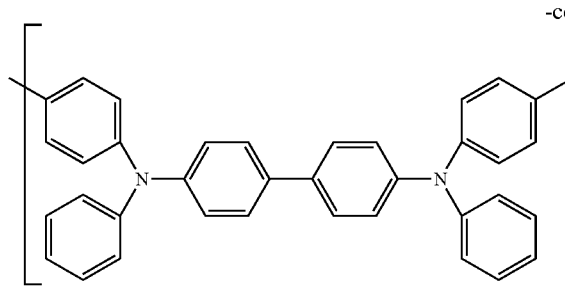
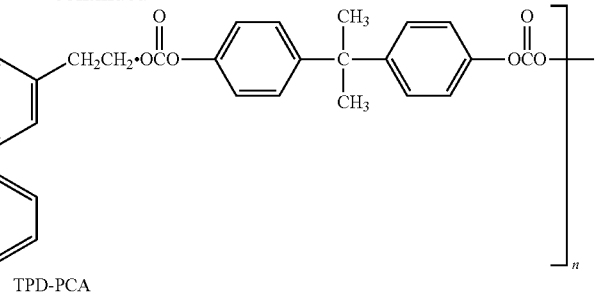

TPD-PCA

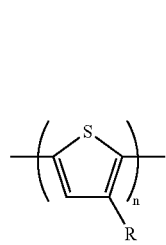

R:$C_6H_{13}$, $C_8H_{17}$, $C_{12}H_{25}$
Poly thiophene

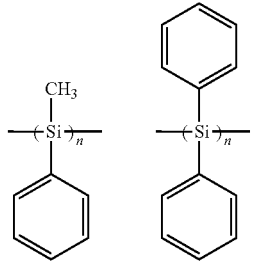

Poly silicone

Polymer light emitting material and electric charge transporting material

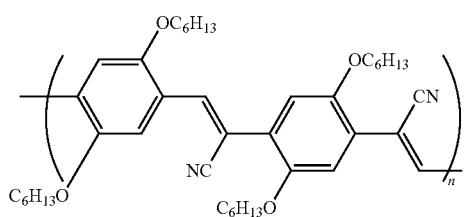

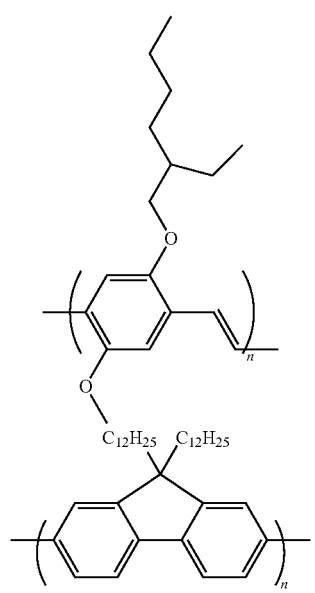

-continued

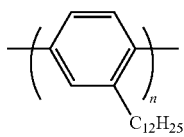
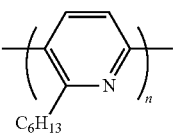

An anode material desirably has a work function as large as possible. Examples of the anode material include a metal such as gold, platinum, nickel, palladium, cobalt, selenium, or vanadium. In addition, each of alloys thereof and metal oxides such as tin oxide, zinc oxide, indium oxide, indium tin oxide (ITO), and indium zinc oxide may be used. Further, a conductive polymer such as polyaniline, polypyrrole, polythiophene, or polyphenylene sulfide may also be used. Each of those electrode substances may be used alone, or two or more of them may be used in combination.

On the other hand, a cathode material desirably has a small work function. Examples of the cathode material include: a metal such as lithium, sodium, potassium, cesium, calcium, magnesium, aluminum, indium, silver, lead, tin, or chromium; and an alloy of plural metals thereof. Alternatively, a metal oxide such as indium tin oxide (ITO) may also be used. Further, a cathode may adopt a single layer structure or a multilayer structure.

A substrate to be used in the present invention is, but not particularly limited to, an opaque substrate such as a metallic substrate or a ceramic substrate, or a transparent substrate of glass, quartz, or a plastic sheet may be used. In addition, a luminescent color may be controlled by using a color filter film, a fluorescent color conversion filter film, a dielectric reflective film, or the like as the substrate.

In the organic light emitting device of the present invention, upon forming a layer containing the carbazole derivative of the present invention or a layer containing another organic compound, a thin film is generally formed by a vacuum vapor deposition method. Alternately, each layer is dissolved into an appropriate solvent to form a thin film by an application method. In particular, when the application method is used, the film may also be formed in combination with an appropriate binder resin.

The binder resin may be selected from a wide variety of binder resins. Examples of the binder resin include, but not limited to these, a polyvinyl carbazole resin, a polycarbonate resin, a polyester resin, a polyarylate resin, a polystyrene resin, an acrylic resin, a methacrylic resin, a butyral resin, a polyvinyl acetal resin, a diallyl phthalate resin, a phenol resin, an epoxy resin, a silicone resin, a polysulfone resin, and a urea resin. Each of those resins may be used alone, or one or two or more kinds may be mixed as a copolymer.

It should be noted that the produced organic light emitting device may be provided with a protective layer or a sealing layer for the purpose of preventing the device from contacting with, for example, oxygen or moisture. Examples of the protective layer include: an inorganic material film such as a diamond thin film, a metal oxide, or a metal nitride; a polymer film such as a fluorine resin, polyparaxylene, polyethylene, a silicone resin, or a polystyrene resin; and a photocurable resin. In addition, the device itself may be covered with, for example, glass, a gas impermeable film, or a metal, and packaged with an appropriate sealing resin.

In the organic light emitting device of the present invention, a thickness of the organic compound layer containing the carbazole derivative of the present invention is preferably 10 μm or less, more preferably, 0.5 μm or less, most preferably, from 0.01 μm to 0.5 μm.

The organic light emitting device of the present invention is preferably an electric field light emitting device that emits light by applying a voltage between the anode and the cathode.

Hereinafter, the present invention will be described more specifically by way of examples. However, the present invention is not limited to these examples.

Example 1

Synthesis of Exemplified Compound No. A-25

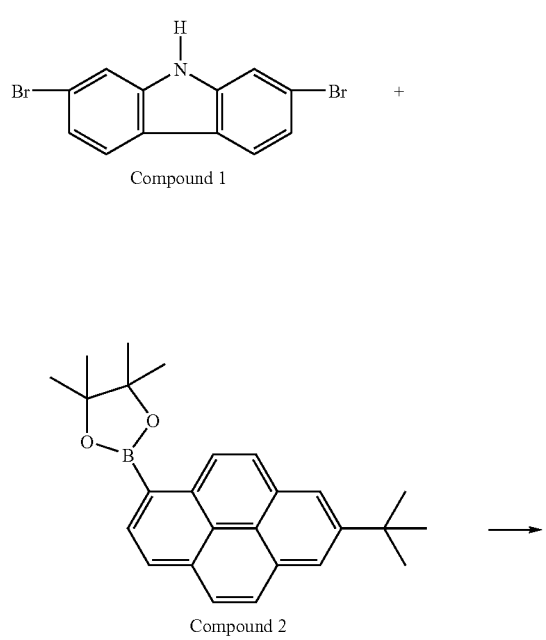

Compound 1

Compound 2

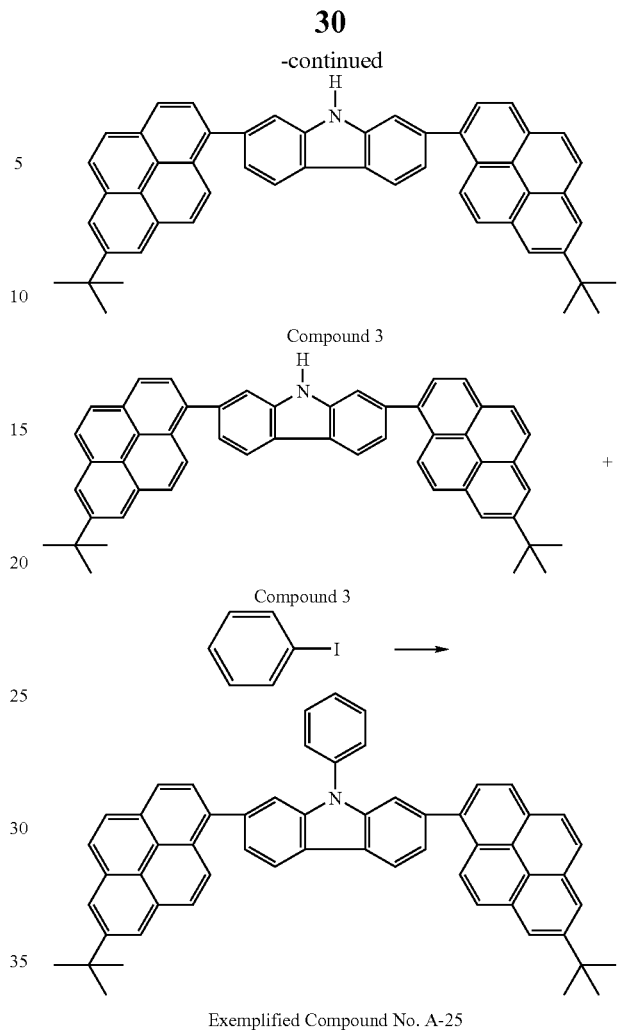

Compound 3

Compound 3

Exemplified Compound No. A-25

Compounds described below were each charged into a 300-ml flask.
Compound 1: 3.25 g (10 mmol)
Compound 2: 7.69 g (20 mmol)
Toluene: 50 ml
Ethanol: 25 ml
2M sodium carbonate solution: 50 ml
Tetrakis(triphenylphosphine)palladium (0): 1 g After the charge, agitation was performed at 80° C. for 8 hours under nitrogen flow. After the reaction, the reaction solution was extracted with toluene, and then the organic layer was washed with water. The organic layer was dried with magnesium sulfate and concentrated under reduced pressure. After the purification by silica gel chromatography (eluent: hexane/chloroform), recrystallization was performed with toluene/ethanol to obtain 5.3 g of Compound 3 (yield: 78.0%).

Next, compounds described below were each charged into a 200-ml flask.
Compound 3: 1.00 g (1.47 mmol)
Iodobenzene: 0.36 g (1.78 mmol)
Ortho-xylene: 70 ml
Tritertiary butylphosphine: 37 mg
Palladium acetate: 7.6 mg
Sodium tertiary buthoxide: 1.44 g After the charge, agitation was performed at 150° C. for 8 hours under nitrogen flow. After the reaction, the reaction solution was extracted with toluene, and then the organic layer was washed with water. The organic layer was dried with magnesium sulfate and concentrated under reduced pressure. After the purification by silica gel chromatography (eluent: hexane/chloroform), recrystallization was performed with toluene/ethanol to obtain 1.02 g of Exemplified Compound No. A-25 (yield: 91.8%).

Matrix-assisted laser desorption/ionization time-of-flight mass spectrometry (MALDI-TOF MS) confirmed that the M+ of the compound was 755.4.

Further, the structure of the compound was confirmed with NMR measurement.

$1^H$ NMR (CDCl$_3$, 500 MHz) δ (ppm): 8.39 (d, 2H), 8.26-8.01 (m, 8H), 8.08 (s, 4H), 8.03 (m, 4H), 7.69 (m, 4H), 7.63 (m, 2H), 7.52 (t, 2H), 7.35 (m, 1H), 1.59 (s, 18H)

It should be noted that Exemplified Compound No. A-26 may be synthesized by the same manner as in Example 1 except that the following compound 6 is used instead of using Compound 2 of Example 1.

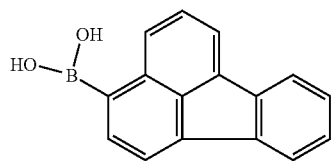

Compound 6

Exemplified Compound No. A-29 may be synthesized by the same manner as in Example 1 except that the following compound 7 is used instead of using Compound 2 of Example 1.

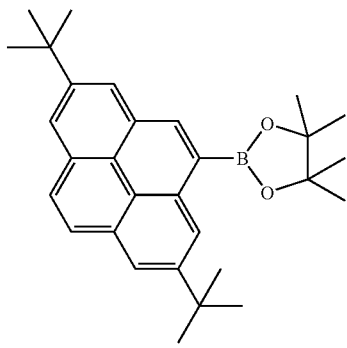

Compound 7

Example 2

Synthesis of Exemplified Compound No. A-35

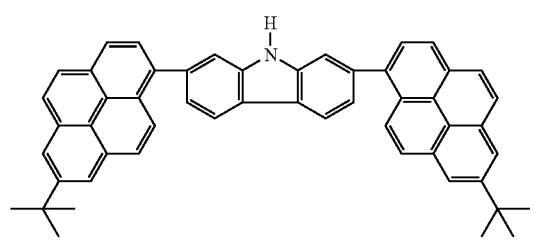

Compound 3

+

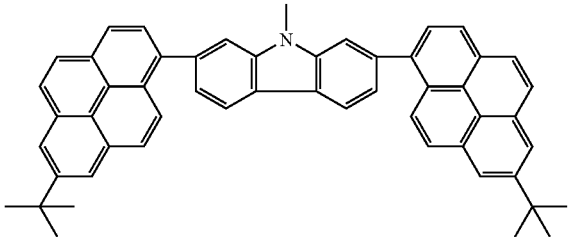

Exemplified Compound No. A-35

1.00 g (1.47 mmol) of Compound 3, 36 mg of sodium hydroxide, 50 ml of dimethylformamide were each charged into a 100-ml flask, and agitation was performed for 1 hour under nitrogen flow. 0.3 g of methyliodide was dropped thereinto, and the agitation was further performed at room temperature for 5 hours. After the completion of the reaction, the reaction solution was added with methanol and dried and concentrated under reduced pressure. The reaction solution was added with water and extracted with toluene, and dried with magnesium sulfate and concentrated under reduced pressure. After the purification by silica gel chromatography (eluent: toluene), recrystallization was performed with toluene/ethanol. The obtained crystal was dried under vacuum and subjected to sublimation purification to obtain 980 mg of Exemplified Compound No. A-35 (yield: 96.1%).

Matrix-assisted laser desorption/ionization time-of-flight mass spectrometry (MALDI-TOF MS) confirmed that the M+ of the compound was 693.3.

Further, the structure of the compound was confirmed with NMR measurement.

$1^H$ NMR (CDCl$_3$, 500 MHz) δ (ppm): 8.34 (d, 2H), 8.29-8.22 (m, 8H), 8.11 (s, 6H), 8.03 (d, 2H), 7.70 (s, 2H), 7.58 (d, 2H), 3.97 (s, 3H), 1.60 (s, 18H)

Example 3

Production of Organic Light Emitting Device

Indium tin oxide (ITO) was formed by a sputtering method into a film having a thickness of 120 nm to serve as the anode on a glass substrate. The substrate on which ITO film was formed was subjected to ultrasonic cleaning with acetone and isopropyl alcohol (IPA) sequentially. Then, the substrate was subjected to boiling cleaning with IPA, followed by UV/ozone cleaning. Thus treated glass substrate was used as a transparent conductive supporting substrate.

Chloroform solution of Compound 4 described below was applied onto the transparent conductive supporting substrate by a spin coating method to form a film into a film thickness of 20 nm, thereby obtaining a hole transporting layer. Next, the other organic layer and the electrode layer were successively formed by vacuum vapor deposition using resistive heating within a vacuum chamber of $10^{-5}$ Pa. Specifically, first, the light emitting layer was formed into a film thickness of 20 nm so that the weight ratio of Exemplified Compound No. A-25 became 10% of the total of Exemplified Compound No. A-25 and Compound 5. Next, as the electron transporting layer, bathophenanthroline (Bphen) (produced by Dojinkagaku Laboratories) represented by the following formula was formed into a film having a film thickness of 30 nm. Then, as a first metal electrode layer, LiF film was formed into a thickness of 0.5 nm. Finally, as a second electrode layer, Al film was formed into a thickness of 150 nm.

As described above, the organic light emitting device of the present invention was produced.

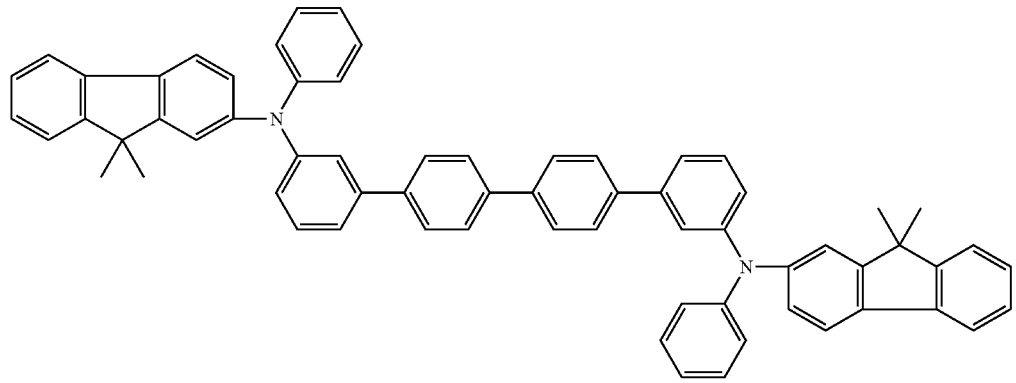

Compound 4

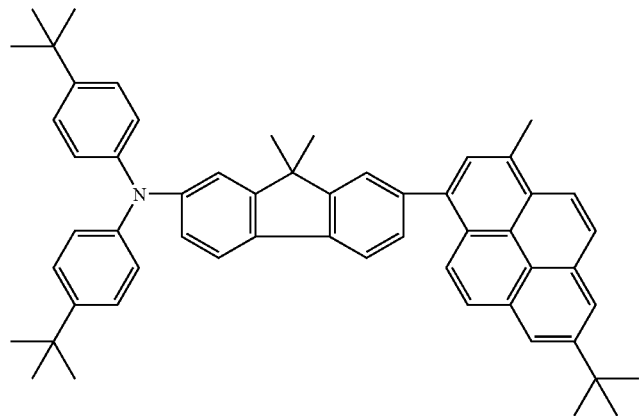

Compound 5

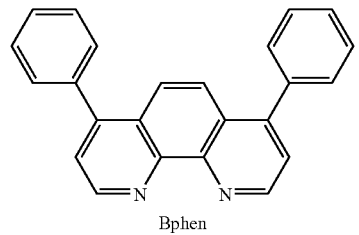

Bphen

The characteristics of the produced organic light emitting device were determined. Specifically, current-voltage characteristic of the device was measured using a microammeter 4140B (manufactured by Hewlett Packard), and light emitting luminance of the device was measured using BM7 (manufactured by Topcon corporation). As a result, the device of Example 3 was observed to emit blue light having an light emitting luminance of 1,720 cd/m² at an applied voltage of 4.5 V. Further, a voltage was applied continuously to the device for 100 hours under a nitrogen atmosphere. As a result, the stable light emission could be obtained after applying the voltage continuously for 100 hours.

Example 4

The organic light emitting device was produced by the same manner as in Example 3 except that Exemplified Compound No. A-35 was used instead of using Exemplified Compound No. A-25 of Example 3. The characteristics of the produced organic light emitting device were measured by the same manner as in Example 3. As a result, the device of Example 4 was observed to emit blue light having a light emitting luminance of 1,610 cd/m² at an applied voltage of 4.5 V. Further, a voltage was applied continuously to the device for 100 hours under a nitrogen atmosphere. As a result, the stable light emission could be obtained after applying the voltage continuously for 100 hours.

As described above, the organic light emitting device of the present invention, in which the carbazole derivative of the present invention is used in the light emitting layer, particularly, as a host, is an excellent light emitting device because the organic light emitting device has not only a light emission with high efficiency but also keep a high luminance for a longer period of time. In addition, the organic light emitting device of the present invention can be produced by vacuum vapor deposition or using a casting method. Consequently, a device with a large area can be produced at a relatively low cost.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-328340, filed Dec. 5, 2006, which is hereby incorporated by reference herein in its entirety.

What is claimed is:

1. A carbazole derivative represented by the following formula:

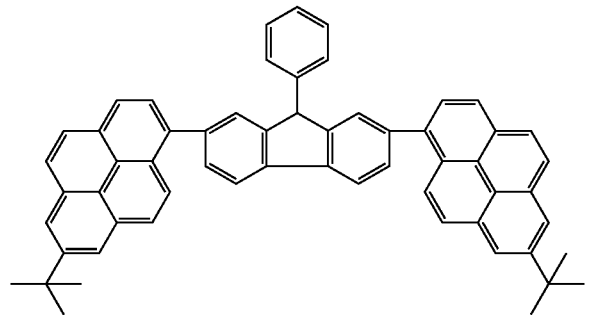

or

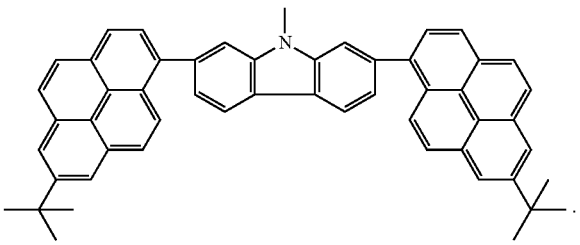

2. An organic light emitting device comprising:
a pair of electrodes including an anode and a cathode; and
an organic compound layer interposed between the pair of electrodes,
wherein the organic compound layer contains at least one kind of the carbazole derivative according to claim 1.

3. The organic light emitting device according to claim 2, wherein the organic compound layer is a light emitting layer.

4. The organic light emitting device according to claim 3, wherein the light emitting layer comprises a host and a guest, and the host and the guest each comprise the carbazole derivative.

5. The organic light emitting device according to claim 2, which comprises an electric field light emitting device that emits light by applying a voltage between the pair of electrodes.

* * * * *